US00PP25469P2

(12) United States Plant Patent
Zampini

(10) Patent No.: US PP25,469 P2
(45) Date of Patent: Apr. 28, 2015

(54) ***CORNUS* PLANT NAMED 'CHOVOZAM'**

(50) Latin Name: *Cornus alba*
Varietal Denomination: Chovozam

(71) Applicant: James W. Zampini, Fairport Harbor, OH (US)

(72) Inventor: James W. Zampini, Fairport Harbor, OH (US)

(73) Assignee: Lake Country Nursery, Perry, OH (US)

( * ) Notice: Subject to any disclaimer, the term of this patent is extended or adjusted under 35 U.S.C. 154(b) by 22 days.

(21) Appl. No.: 13/815,637

(22) Filed: Mar. 13, 2013

(51) Int. Cl.
*A01H 5/00* (2006.01)

(52) U.S. Cl.
USPC ..... Plt./220

(58) Field of Classification Search
USPC ..... Plt./220
See application file for complete search history.

*Primary Examiner* — Annette Para
(74) *Attorney, Agent, or Firm* — Penny J. Aguirre

(57) ABSTRACT

A new cultivar of *Cornus*, 'Chovozam', that is characterized by its thick variegated foliage with green centers and creamy white margins that becomes tinged with red in the fall, its stems that are bright red in winter, its upright rounded and very compact plant habit, its bright white fruit, its creamy white flowers, and its slow growth habit.

2 Drawing Sheets

Botanical classification: *Cornus alba.*
Variety denomination: 'Chovozam'.

BACKGROUND OF THE INVENTION

The present invention relates to a new and distinct cultivar of *Cornus alba*, and will be referred to hereafter by its cultivar name, 'Chovozam'. 'Chovozam' is a new cultivar of red twig dogwood, a shrub grown for use as an ornamental landscape plant.

The Inventor discovered the new cultivar as naturally occurring whole plant mutation in a seedbed at his nursery in Perry, Ohio in 2009. The seedbed had been planted with seeds from an unnamed plant of *Cornus alba.*

Asexual propagation of the new cultivar was first accomplished by the Inventor using stem cuttings in summer of 2009 in Perry, Ohio. Asexual propagation of the new cultivar by stem cuttings has been determined that the characteristics are stable and are reproduced true to type in successive generations.

SUMMARY OF THE INVENTION

The following traits have been repeatedly observed and represent the characteristics of the new cultivar as grown outdoors in a trial plot in Perry, Ohio. These attributes in combination distinguish 'Chovozam' as unique cultivar of *Cornus.*

1. 'Chovozam' exhibits thick variegated foliage with green centers and creamy white margins and becoming tinged with red in early to late summer into fall.
2. 'Chovozam' exhibits stems that are bright red in winter.
3. 'Chovozam' exhibits an upright and rounded and very compact plant habit.
4. 'Chovozam' exhibits bright white fruit.
5. 'Chovozam' exhibits creamy white flowers.
6. 'Chovozam' exhibits a slow growth rate.

The parent plant of 'Chovozam' differs from 'Chovozam' in having thinner leaves, in having a more vigorous growth habit, a less compact plant habit and less bright red stems, and in lacking early pink coloration to the foliage, 'Chovozam' can be most closely compared to the cultivars of *Cornus alba*, 'Bailhalo' (U.S. Plant Pat. No. 8,722) and 'Stdazam' (not patented). Both cultivars differ from 'Chovozam' in having plant habits that are less compact, leaves that are thinner and larger, centers that are lighter green, and that develop a red tinge later in the fall.

BRIEF DESCRIPTION OF THE DRAWING

The accompanying colored photographs were taken in mid summer and illustrate the overall appearance and distinct characteristics of 3 year-old plants the new *Cornus* as grown in a garden in Perry, Ohio.

The photograph in FIG. 1 provides a view of the plant habit of 'Chovozam'.

Figure 1:
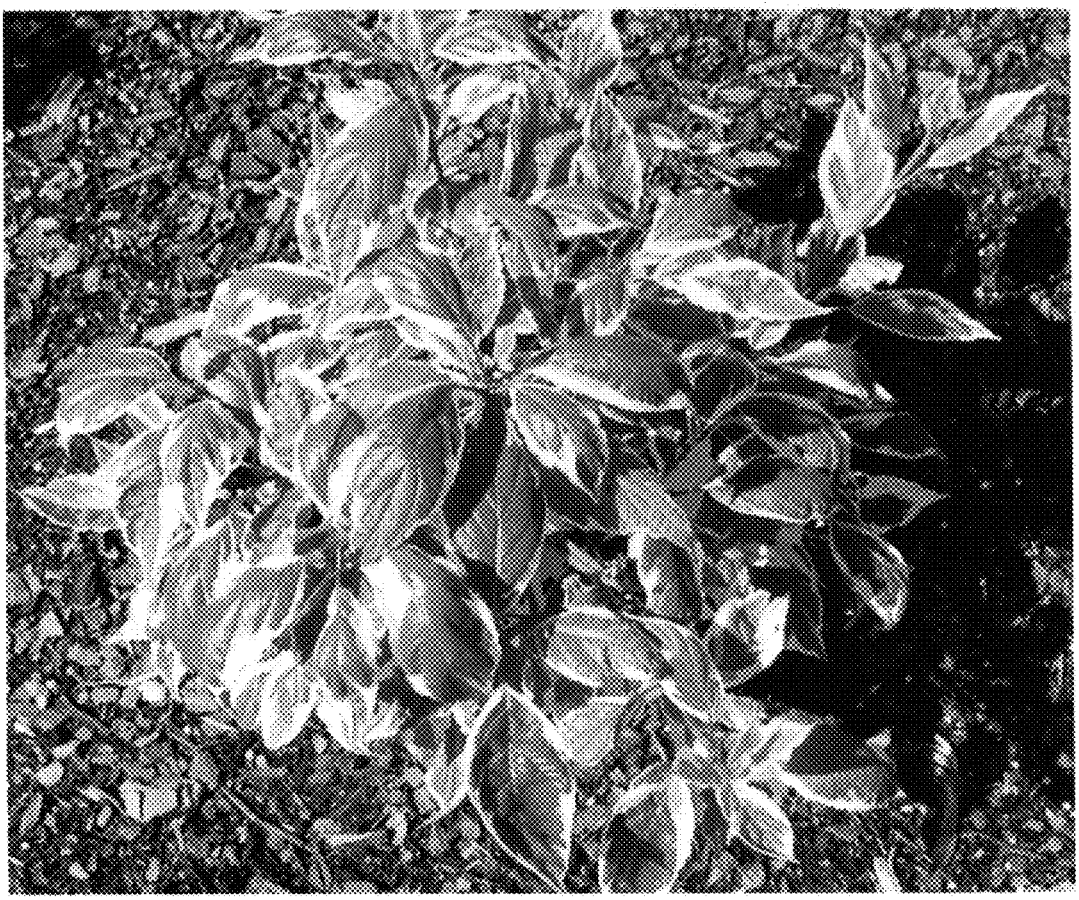
Figure 2:
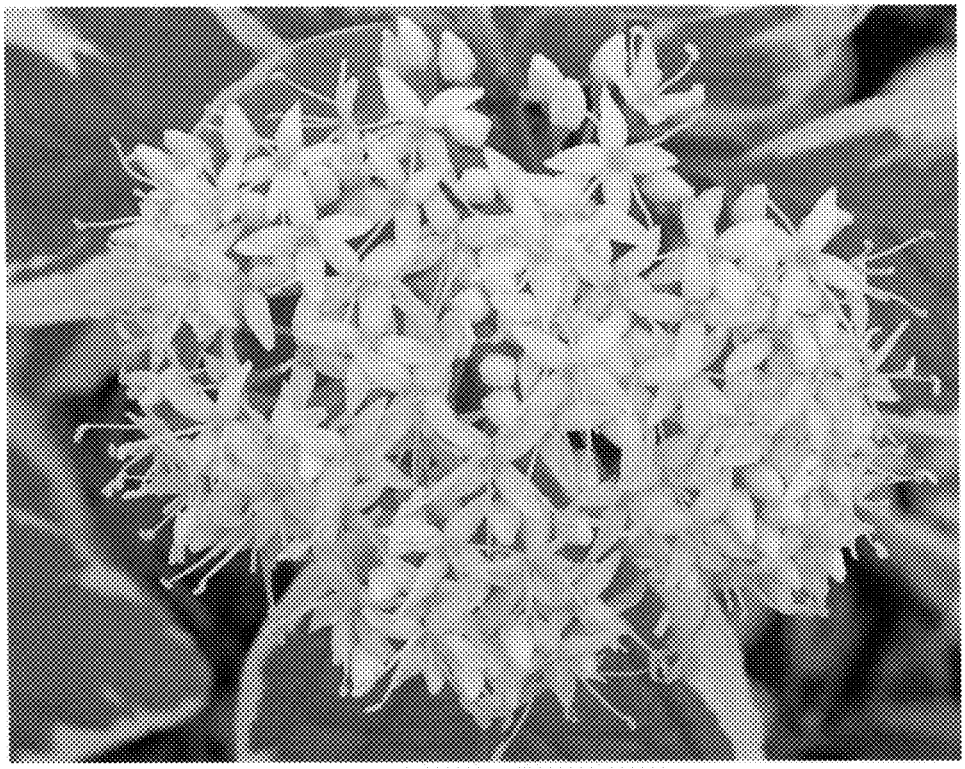

The photograph in FIG. 2 provides a close-up view of an inflorescence of 'Chovozam'.

Figure 3:
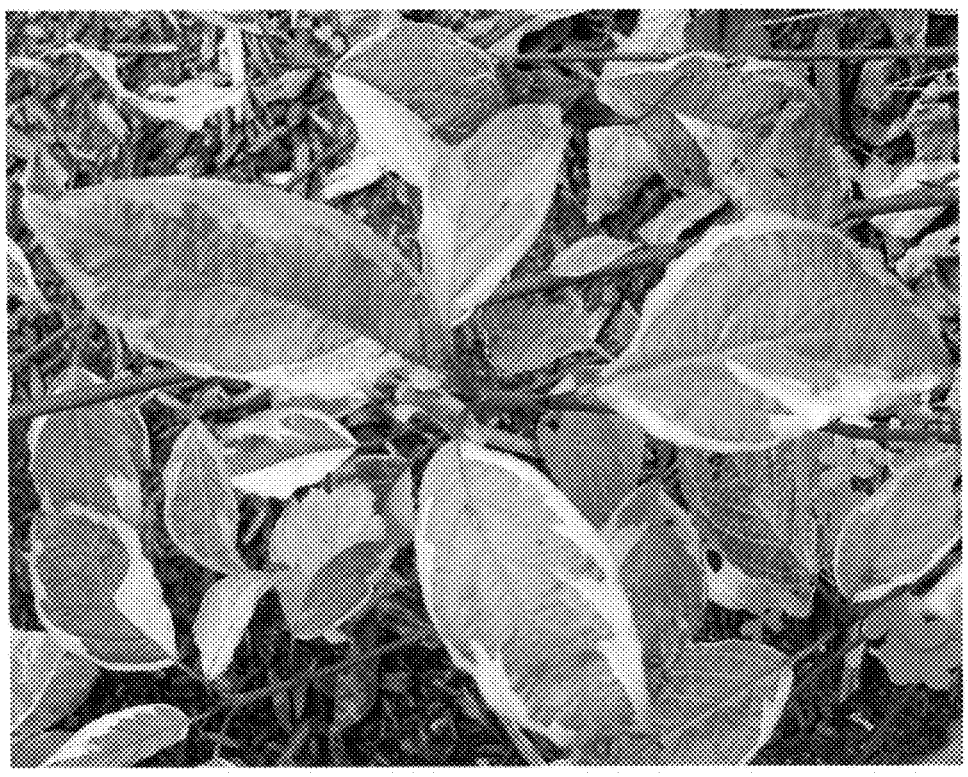

The photograph in FIG. 3 provides a view of the fall foliage of 'Chovozam'.

The colors in the photographs may differ slightly from the color values cited in the detailed botanical description, which accurately describe the colors of the new *Cornus.*

DETAILED BOTANICAL DESCRIPTION

The following is a detailed description of 2 year-old plants the new *Cornus* as grown in 2-gallon containers in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms late spring/early summer in Northeastern Ohio.

*Plant type.*—Deciduous shrub.

*Plant habit*.—Upright and rounded, very compact, suckering.

*Plant height and spread*.—Reaches 0.9 to 1.2 m in height and 0.6 to 0.9 m in spread in the landscape for three years.

*Diseases and pests*.—The new cultivar has been observed to be disease free to date under the trial conditions grown.

*Cold hardiness*.—At least in U.S.D.A. Zone 4.

*Root description*.—Fibrous.

*Propagation*.—Softwood (preferred) or hardwood stem cuttings.

*Growth rate*.—Slow.

Stem description:

*Shape*.—New growth; hexagonal, mature stem; rounded.

*Stem color*.—New growth; 144A with a slight blend of 183B, maturing wood; 144A overlaid with 183B, bark N199B, winter 183B.

*Stem size*.—Main branches; about 0.5 cm in diameter measured 4.0 cm above the soil level, lateral branches; average of 2.0 mm in diameter and 10.5 to 27 cm in length.

*Stem surface*.—New growth and mature stems glabrous lightly spotted with lenticels 160C in color.

*Internode length*.—Up to 3.5 cm in length.

*Branching*.—An average of 1 to 3 basal stems, with up to 4 lateral branches, an average of 1 to 4 per basal stem.

Foliage description:

*Leaf shape*.—Elliptic.

*Leaf division*.—Simple.

*Leaf base*.—Cuneate.

*Leaf apex*.—Acuminate to Acute.

*Leaf fragrance*.—None.

*Leaf venation*.—Pinnate, not conspicuous, color matches leaf coloration on upper surface and lower surface.

*Leaf margins*.—Slightly crenate with undulations to entire.

*Leaf substance*.—Thin.

*Leaf arrangement*.—Opposite.

*Leaf attachment*.—Petiolate.

*Leaf surface*.—Glabrous to very slightly pubescent upper and lower surface with new growth shiny on upper surface and pubescent on upper and lower surface.

*Leaf color*.—Newly expanded leaves upper and lower surface; mostly 149D with random slight overlays of 184A towards the edges of the margins and randomly suffused with 146A in the center, mature leaves upper surface; centers 138A, margins NN155A, fading to a slight overlay of 184A towards the tips, mature leaves lower surface; centers 138B, margins NN155A, color early to late summer into fall upper surface; centers 138A and suffused with 70C , margins 70C and 69A, color early to late summer into fall lower surface; centers 138A and suffused with 70C, margins 70C and 69A.

*Petioles*.—About 2 cm in length and 1.5 mm in width, 146A, with an overlay of 187B in color, glabrous surface.

*Stipules*.—About 2.1 mm in length and 0.9 mm in width, apex; acute and 187C in color, base; a blend of 144B.

Inflorescence description:

*Inflorescence type*.—Compound corymb on terminals.

*Inflorescence size*.—An average of 4 cm in length and 6 cm in diameter.

*Flower buds*.—Ovate in shape, NN155A in color, an average of 4.5 mm in length and 3 mm in width.

*Flower fragrance*.—None.

*Lastingness of inflorescence*.—Inflorescence blooms for 10 days with individual flowers lasting about 4 days.

*Flower quantity*.—Average of 150 flowers per inflorescence.

*Flower type*.—Rotate (star-shaped).

*Flower size*.—Average of 9 mm in diameter and 5.5 mm in depth.

*Peduncles*.—Primary an average of 1.5 cm in length to base of inflorescence and 3 mm in diameter with secondary an average of 1 cm in length and 2 mm in width and tertiary an average of 8 mm in length and 1.5 mm in width, 144A in color, glabrous to slightly pubescent surface, oval in shape.

*Pedicels*.—Average of 2.5 mm in length to base of inflorescence and 1.5 mm in diameter, 144A in color, glaucous surface, oval in shape.

*Calyx*.—Closed campanulate in shape, 1.6 mm in diameter and 2 mm in depth.

*Sepals*.—4, entirely fused into calyx, 144A in color, finely pubescent surface.

*Petals*.—4, base fused to top of calyx, spreading horizontally, lanceolate in shape, 4 mm in length and 2 mm in width, margins entire, apex acute, outer and inner surface is glabrous, color of inner and outer surface is NN155B.

Reproductive organs:

*Gynoecium*.—1 pistil, style is about 2 mm in length, and 145D in color, stigma is about 0.7 mm in diameter, globose in shape and 145D in color, ovary is disked shape, about 1.5 mm in diameter and 145C in color.

*Androcoecium*.—4 stamens, about 7 mm in length, all exserted beyond corolla, filaments are 157C in color and about 5.5 mm in length, anthers are about 1.5 mm in length, dorsifixed, 162D in color, pollen is moderate in quantity and 4D in color.

*Fruit and seed*.—True berry, oblong in shape, about 1 cm in length and 7 mm in diameter, present in mid summer, matures to 157D in color, seed; 1, 6 mm in length and 4 mm in width in size and 199A in color.

It is claimed:

1. A new and distinct cultivar of *Cornus* plant named 'Chovozam' as herein illustrated and described.

* * * * *